United States Patent
Granger

(10) Patent No.: US 10,520,752 B2
(45) Date of Patent: Dec. 31, 2019

(54) METHOD FOR DETERMINING AN OPTICAL FUNCTION OF AN OPHTHALMIC LENS ADAPTED TO A WEARER

(71) Applicant: Essilor International, Charenton-le-Pont (FR)

(72) Inventor: Berangere Granger, Charenton-le-Pont (FR)

(73) Assignee: Essilor International, Charenton-le-Pont (FR)

( * ) Notice: Subject to any disclaimer, the term of this patent is extended or adjusted under 35 U.S.C. 154(b) by 58 days.

(21) Appl. No.: 15/560,116

(22) PCT Filed: Mar. 8, 2016

(86) PCT No.: PCT/EP2016/054855
§ 371 (c)(1),
(2) Date: Sep. 20, 2017

(87) PCT Pub. No.: WO2016/150692
PCT Pub. Date: Sep. 29, 2016

(65) Prior Publication Data
US 2018/0101023 A1    Apr. 12, 2018

(30) Foreign Application Priority Data

Mar. 20, 2015    (EP) .................................... 15305410

(51) Int. Cl.
| | |
|---|---|
| *G02C 7/00* | (2006.01) |
| *G02C 7/02* | (2006.01) |
| *A61B 3/00* | (2006.01) |
| *A61B 3/036* | (2006.01) |
| *A61B 5/12* | (2006.01) |
| *G02C 7/10* | (2006.01) |
| *G02C 7/06* | (2006.01) |

(52) U.S. Cl.
CPC ............ *G02C 7/027* (2013.01); *A61B 3/0025* (2013.01); *A61B 3/036* (2013.01); *A61B 5/123* (2013.01); *G02C 7/104* (2013.01); *G02C 7/061* (2013.01)

(58) Field of Classification Search
CPC ........ G02C 7/024; G02C 7/025; G02C 7/027; G02C 7/028

USPC .......................... 351/159.03, 159.39, 159.4, 351/159.73–159.77
See application file for complete search history.

(56) References Cited

U.S. PATENT DOCUMENTS

| | | | | |
|---|---|---|---|---|
| 5,002,382 A | * | 3/1991 | Seidner | G02C 7/027 |
| | | | | 351/159.41 |
| 6,155,681 A | * | 12/2000 | Kris | G02C 7/06 |
| | | | | 351/159.42 |
| 7,506,977 B1 | | 3/2009 | Aiiso | |
| 2011/0007266 A1 | * | 1/2011 | Blum | G02C 7/06 |
| | | | | 351/159.42 |
| 2012/0035430 A1 | * | 2/2012 | Roth | A61H 39/00 |
| | | | | 600/300 |

FOREIGN PATENT DOCUMENTS

| | | |
|---|---|---|
| FR | 2844365 A1 | 3/2004 |
| KR | 20140091195 A | 7/2014 |
| WO | 2010072840 A1 | 7/2010 |

OTHER PUBLICATIONS

Nabelek, et al.; "Comparison of Speech Perception in Background Noise with Acceptance of Background Noise in Aided and Unaided Conditions"; Journal of Speech, Language, and Hearing Research; Oct. 2014; vol. 47; p. 1001-1011.

Hidalgo, et al.; "The Hearing-Dependent Daily Activities Scale to Evaluate Impact of Hearing Loss in Older People"; Annals of Family Medicine; Sep./Oct. 2008; vol. 6 No. 5; pp. 441-447.

ISR/WO for International Application No. PCT/EP2016/054855 dated Jun. 9, 2016.

* cited by examiner

*Primary Examiner* — Darryl J Collins
(74) *Attorney, Agent, or Firm* — Oblon, McClelland, Maier & Neustadt, L.L.P.

(57) ABSTRACT

A method implemented by computer means for determining an optical function of an ophthalmic lens adapted to a wearer, the method comprising:
  a wearer data providing step, during which wearer data comprising at least an indication of the hearing sensitivity of the wearer and an indication of the ophthalmic prescription of the wearer are provided,
  an optical function determining step, during which an optical function adapted to the wearer is determined based at least on the wearer data.

15 Claims, 9 Drawing Sheets

METHOD FOR DETERMINING AN OPTICAL FUNCTION OF AN OPHTHALMIC LENS ADAPTED TO A WEARER

FIELD OF THE INVENTION

The invention relates to a method implemented by computer means for determining an optical function of an ophthalmic lens adapted to a wearer. The invention further relates to the use of an ophthalmic lens comprising at least a zone adapted for intermediate distance vision for increasing the understanding by the wearer of the ophthalmic lens of a vocal message.

BACKGROUND OF THE INVENTION

Usually, when a person has difficulty for hearing, this person goes to the premise of a physician to carry out hearing tests so as to provide a hearing aid device.

Typically, the hearing aid or deaf aid devices are electroacoustic devices which are designed to amplify sound for the wearer, usually with the aim of making speech more intelligible, and to correct impaired hearing as measured by audiometry.

Such hearing aid device although efficient, presents some drawbacks as the fact of presenting a discomfort to the wearer, requires to be powered by an electrical source, may interfere with other electronic devices such as phone, radio etc. . . .

Therefore, there is a need for an adapted device that could either replace the existing hearing device or increase the hearing aid for the wearer.

One object of the present invention is to provide such an adapted device.

SUMMARY OF THE INVENTION

To this end, the invention proposes a method, for example implemented by computer means, for determining an optical function of an ophthalmic lens adapted to a wearer, the method comprising:
- a wearer data providing step, during which wearer data comprising at least an indication of the hearing sensitivity of the wearer and an indication of the ophthalmic prescription of the wearer are provided,
- an optical function determining step, during which an optical function adapted to the wearer is determined based at least on the wearer data.

The method according to the invention, proposes to determine the hearing sensitivity of the wearer and choosing an adapted optical design according to this sensitivity.

Advantageously, the method according to the invention allows identifying wearers with hearing discomfort and offers them a suitable design for their audiovisual needs. The method of the invention may also be used to make speech more intelligible for a wearer having no hearing discomfort.

The solution of the invention has the advantage of improving the auditory comfort of the wearer through a single device and avoiding the discomfort of integrated hearing aid device with glasses equipment (weight, fit, aesthetics . . . ).

The inventors have found that adapting the optical function of the ophthalmic lenses provided to a wearer based on an indication of the hearing sensitivity of the wearer increases significantly the level of understanding of a vocal message, in particular of a speech issued by a person facing the wearer.

According to Further Embodiments which can be Considered Alone or in Combination:
- the wearer data further comprise an indication of the impact of visual indication on the understanding by said wearer of a vocal message; and/or
- said optical function determining step is carried out so that said optical function comprises a zone adapted for facilitating labo-facial reading of the wearer; and/or
- the hearing sensitivity of the wearer provided during wearer data providing step is determined by at least an objective type test; and/or
- said objective type test is a perception test of a range of tonal or vocal frequencies; and/or
- the hearing sensitivity of the wearer provided during wearer data providing step is determined by at least a subjective type test; and/or
- said subjective type test is chosen among one of the following tests consisting of:
  - Evaluation of speech understanding in a noisy environment;
  - Life Questionnaire concerning the hearing in everyday listening situations;
  - Labo-facial reading test; and/or
- said optical function determining step comprises a step of selection of an optical function from a set of predefined optical functions based on said wearer data; and/or
- said optical function determining step comprises a step of determining a transmission function based on said wearer data; and/or
- said optical function determining step comprises a step of determining a dioptric function based on said wearer data.

According to a further aspect, the invention relates to the use of an ophthalmic lens comprising at least a zone adapted for intermediate distance vision for increasing the understanding by the wearer of the ophthalmic lens of a vocal message, for example a vocal message issued by a person facing the wearer.

According to a further aspect, the invention relates to an ophthalmic lens comprising at least a zone adapted for intermediate distance vision for increasing the understanding by the wearer of the ophthalmic lens of a vocal message, for example a vocal message issued by a person facing the wearer.

The invention further relates to an ophthalmic lens adapted for a wearer comprising at least an intermediate distance vision zone adapted for intermediate distance vision, wherein a transmission function of the ophthalmic lens is arranged so as to enhance labo-facial reading of the wearer, for example to enhance the visibility of the lips of a person seen through the intermediate distance vision zone.

According to an embodiment, the ophthalmic lens may be tinted so as to enhance the contrast of the lips of a person seen through the ophthalmic lens.

The invention further comprises a pair of ophthalmic lenses adapted for a wearer, wherein at least one of lenses is has an optical function determined by a method according to the invention.

The invention further relates to a computer program product comprising one or more stored sequences of instructions that are accessible to a processor and which, when executed by the processor, causes the processor to carry out the steps of the methods according to the invention.

The invention also relates to a computer-readable storage medium having a program recorded thereon; where the program makes the computer execute the method of the invention.

The invention further relates to a device comprising a processor adapted to store one or more sequence of instructions and to carry out at least one of the steps of the method according to the invention.

Unless specifically stated otherwise, as apparent from the following discussions, it is appreciated that throughout the specification discussions utilizing terms such as "computing", "calculating", or the like, refer to the action and/or processes of a computer or computing system, or similar electronic computing device, that manipulate and/or transform data represented as physical, such as electronic, quantities within the computing system's registers and/or memories into other data similarly represented as physical quantities within the computing system's memories, registers or other such information storage, transmission or display devices.

Embodiments of the present invention may include apparatuses for performing the operations herein. These apparatuses may be specially constructed for the desired purposes, or it may comprise a general purpose computer or Digital Signal Processor ("DSP") selectively activated or reconfigured by a computer program stored in the computer. Such a computer program may be stored in a computer readable storage medium, such as, but is not limited to, any type of disk including floppy disks, optical disks, CD-ROMs, magnetic-optical disks, read-only memories (ROMs), random access memories (RAMs) electrically programmable read-only memories (EPROMs), electrically erasable and programmable read only memories (EEPROMs), magnetic or optical cards, or any other type of media suitable for storing electronic instructions, and capable of being coupled to a computer system bus.

The processes and displays presented herein are not inherently related to any particular computer or other apparatus. Various general purpose systems may be used with programs in accordance with the teachings herein, or it may prove convenient to construct a more specialized apparatus to perform the desired method. The desired structure for a variety of these systems will appear from the description below. In addition, embodiments of the present invention are not described with reference to any particular programming language. It will be appreciated that a variety of programming languages may be used to implement the teachings of the inventions as described herein.

BRIEF DESCRIPTION OF THE DRAWINGS

Embodiments of the invention will now be described, by way of example only, and with reference to the following drawings in which.

DETAILED DESCRIPTION OF PREFERRED EMBODIMENTS

Figure 1:
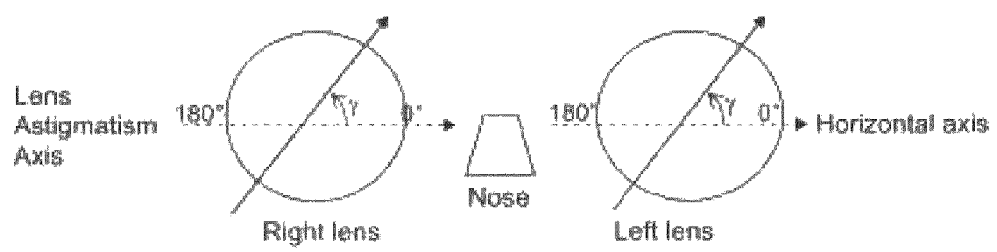
FIG. 1 illustrates the astigmatism axis γ of a lens in the TABO convention.

In the sense of the invention, an optical function corresponds to a function providing for each gaze direction the effect of an ophthalmic lens on the light ray passing through the ophthalmic lens.

The optical function may comprise dioptric function, light absorption, polarizing capability, reinforcement of contrast capacity, etc. ...

The dioptric function corresponds to the ophthalmic lens power (mean power, astigmatism etc. ...) as a function of the gaze direction.

The wording "optical design" is a widely used wording known from the man skilled in the art in ophthalmic domain to designate the set of parameters allowing to define a dioptric function of an ophthalmic lens; each ophthalmic lens designer has its own designs, particularly for progressive ophthalmic lenses. As for an example, a progressive ophthalmic lens "design" results of an optimization of a progressive surface so as to restore a presbyope's ability to see clearly at all distances but also to optimally respect all physiological visual functions such as foveal vision, extra-foveal vision, binocular vision and to minimize unwanted astigmatisms. For example, a progressive lens design comprises:

a power profile along the main gaze directions (meridian line) used by the lens wearer during day life activities, distributions of powers (mean power, astigmatism, ...) on the sides of the lens, that is to say away from the main gaze direction.

These optical characteristics are part of the "designs" defined and calculated by ophthalmic lens designers and that are provided with the progressive lenses.

Although the invention is not limited to progressive lenses, the wording used is illustrated in figures for a progressive lens. The skilled person can adapt the definitions in case of single vision lenses.

A progressive lens comprises at least one but preferably two non-rotationally symmetrical aspheric surfaces, for instance but not limited to, progressive surface, regressive surface, toric or atoric surfaces.

As is known, a minimum curvature $CURV_{min}$ is defined at any point on an aspherical surface by the formula:

$$CURV_{min} = \frac{1}{R_{max}}$$

where $R_{max}$ is the local maximum radius of curvature, expressed in meters and $CURV_{min}$ is expressed in dioptres.

Similarly, a maximum curvature $CURV_{max}$ can be defined at any point on an aspheric surface by the formula:

$$CURV_{max} = \frac{1}{R_{min}}$$

where $R_{min}$ is the local minimum radius of curvature, expressed in meters and $CURV_{max}$ is expressed in dioptres.

It can be noticed that when the surface is locally spherical, the local minimum radius of curvature $R_{min}$ and the local maximum radius of curvature $R_{max}$ are the same and, accordingly, the minimum and maximum curvatures $CURV_{min}$ and $CURV_{max}$ are also identical. When the surface is aspherical, the local minimum radius of curvature $R_{min}$ and the local maximum radius of curvature $R_{max}$ are different.

From these expressions of the minimum and maximum curvatures $CURV_{min}$ and $CURV_{max}$, the minimum and maximum spheres labeled $SPH_{min}$ and $SPH_{max}$ can be deduced according to the kind of surface considered.

When the surface considered is the object side surface (also referred to as the front surface), the expressions are the following:

$$SPH_{min} = (n-1)*CURV_{min} = \frac{n-1}{R_{max}}, \text{ and}$$

$$SPH_{min} = (n-1)*CURV_{min} = \frac{n-1}{R_{max}}$$

where n is the index of the constituent material of the lens.

If the surface considered is an eyeball side surface (also referred to as the back surface), the expressions are the following:

$$SPH_{min} = (1-n)*CURV_{min} = \frac{1-n}{R_{max}} \text{ and}$$

$$SPH_{max} = (1-n)*CURV_{max} = \frac{1-n}{R_{min}}$$

where n is the index of the constituent material of the lens.

As is well known, a mean sphere $SPH_{mean}$ at any point on an aspherical surface can also be defined by the formula:

$$SPH_{mean} = \frac{1}{2}(SPH_{min} + SPH_{max})$$

The expression of the mean sphere therefore depends on the surface considered:

if the surface is the object side surface, $$SPH_{mean} = \frac{n-1}{2}\left(\frac{1}{R_{min}} + \frac{1}{R_{max}}\right)$$

if the surface is an eyeball side surface, $$SPH_{mean} = \frac{1-n}{2}\left(\frac{1}{R_{min}} + \frac{1}{R_{max}}\right)$$

a cylinder CYL is also defined by the formula $CYL=|SPH_{max}-SPH_{min}|$.

The characteristics of any aspherical face of the lens may be expressed by the local mean spheres and cylinders. A surface can be considered as locally aspherical when the cylinder is at least 0.25 diopters.

Figure 2:
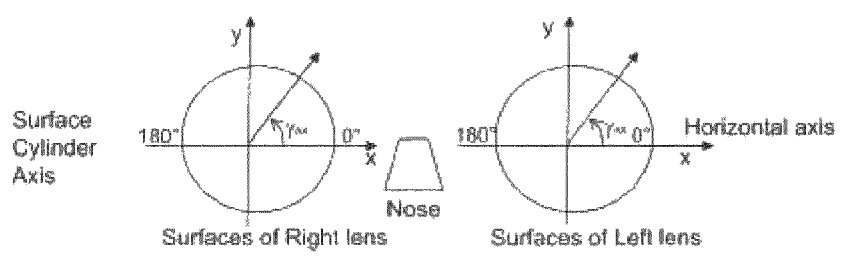
FIG. 2 illustrates the cylinder axis $\gamma_{AX}$ in a convention used to characterize an aspherical surface.

For an aspherical surface, a local cylinder axis $\gamma_{AX}$ may further be defined. FIG. 1 illustrates the astigmatism axis γ as defined in the TABO convention and FIG. 2 illustrates the cylinder axis $\gamma_{AX}$ in a convention defined to characterize an aspherical surface.

The cylinder axis $\gamma_{AX}$ is the angle of the orientation of the maximum curvature $CURV_{max}$ with relation to a reference axis and in the chosen sense of rotation. In the above defined convention, the reference axis is horizontal (the angle of this reference axis is 0°) and the sense of rotation is counterclockwise for each eye, when looking at the wearer ($0° \leq \gamma_{AX} \leq 180°$). An axis value for the cylinder axis $\gamma_{AX}$ of +45° therefore represents an axis oriented obliquely, which when looking at the wearer, extends from the quadrant located up on the right to the quadrant located down on the left.

Moreover, a progressive multifocal lens may also be defined by optical characteristics, taking into consideration the situation of the person wearing the lenses.

Figure 3:
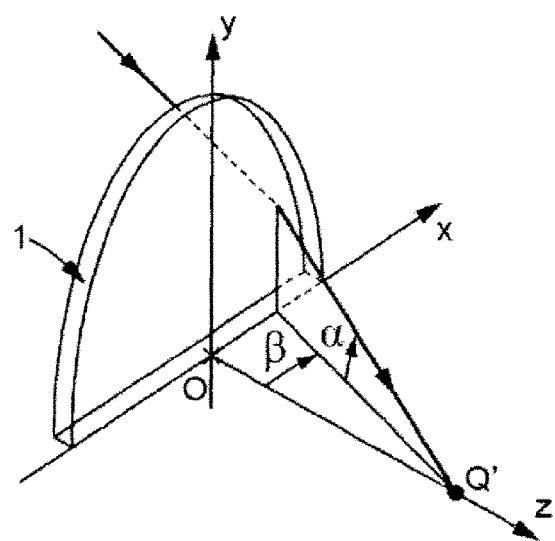
FIGS. 3 and 4 show, diagrammatically, optical systems of eye and lens.
Figure 4:
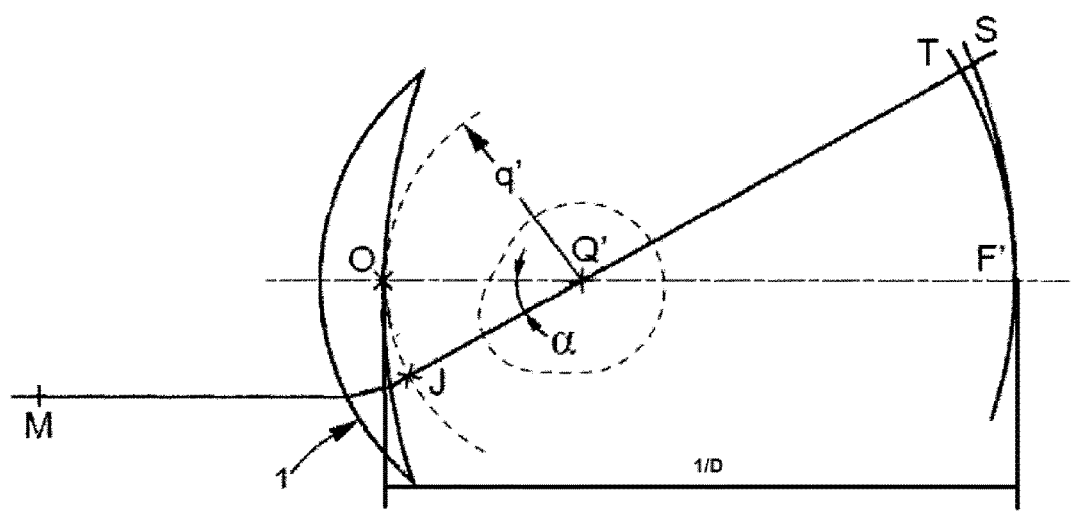

FIGS. 3 and 4 are diagrammatic illustrations of optical systems of eye and lens, thus showing the definitions used in the description. More precisely, FIG. 3 represents a perspective view of such a system illustrating parameters α and β used to define a gaze direction. FIG. 4 is a view in the vertical plane parallel to the antero-posterior axis of the wearer's head and passing through the center of rotation of the eye in the case when the parameter β is equal to 0.

The center of rotation of the eye is labeled Q'. The axis Q'F', shown on FIG. 4 in a dot-dash line, is the horizontal axis passing through the center of rotation of the eye and extending in front of the wearer—that is the axis Q'F' corresponding to the primary gaze view. This axis cuts the aspherical surface of the lens on a point called the fitting cross, which is present on lenses to enable the positioning of lenses in a frame by an optician. The point of intersection of the rear surface of the lens and the axis Q'F' is the point O. O can be the fitting cross if it is located on the rear surface. An apex sphere, of center Q', and of radius q', is tangential to the rear surface of the lens in a point of the horizontal axis. As examples, a value of radius q' of 25.5 mm corresponds to a usual value and provides satisfying results when wearing the lenses.

A given gaze direction—represented by a solid line on FIG. 3—corresponds to a position of the eye in rotation around Q' and to a point J of the apex sphere; the angle β is the angle formed between the axis Q'F' and the projection of the straight line Q'J on the horizontal plane comprising the axis Q'F'; this angle appears on the scheme on FIG. 3. The angle α is the angle formed between the axis Q'J and the projection of the straight line Q'J on the horizontal plane comprising the axis Q'F'; this angle appears on the scheme on FIGS. 3 and 4. A given gaze view thus corresponds to a point J of the apex sphere or to a couple (α, β). The more the value of the lowering gaze angle is positive, the more the gaze is lowering and the more the value is negative, the more the gaze is rising.

In a given gaze direction, the image of a point M in the object space, located at a given object distance, is formed between two points S and T corresponding to minimum and maximum distances JS and JT, which would be the sagittal and tangential local focal lengths. The image of a point in the object space at infinity is formed, at the point F'. The distance D corresponds to the rear frontal plane of the lens.

Ergorama is a function associating to each gaze direction the usual distance of an object point. Typically, in far vision following the primary gaze direction, the object point is at infinity. In near vision, following a gaze direction essentially corresponding to an angle α of the order of 35° and to an angle β of the order of 5° in absolute value toward the nasal side, the object distance is of the order of 30 to 50 cm. For more details concerning a possible definition of an ergorama, U.S. Pat. No. 6,318,859 may be considered. This document describes an ergorama, its definition and its modeling method. For a method of the invention, points may be at infinity or not. Ergorama may be a function of the wearer's ametropia or wearer's addition.

Using these elements, it is possible to define a wearer optical power and astigmatism, in each gaze direction. An object point M at an object distance given by the ergorama is considered for a gaze direction ($\alpha$, $\beta$). An object proximity ProxO is defined for the point M on the corresponding light ray in the object space as the inverse of the distance MJ between point M and point J of the apex sphere:

Prox$O$=1/$MJ$

This enables to calculate the object proximity within a thin lens approximation for all points of the apex sphere, which is used for the determination of the ergorama. For a real lens, the object proximity can be considered as the inverse of the distance between the object point and the front surface of the lens, on the corresponding light ray.

For the same gaze direction ($\alpha$, $\beta$), the image of a point M having a given object proximity is formed between two points S and T which correspond respectively to minimal and maximal focal distances (which would be sagittal and tangential focal distances). The quantity ProxI is called image proximity of the point M:

$$Prox I = \frac{1}{2}\left(\frac{1}{JT} + \frac{1}{JS}\right)$$

By analogy with the case of a thin lens, it can therefore be defined, for a given gaze direction and for a given object proximity, i.e. for a point of the object space on the corresponding light ray, an optical power Pui as the sum of the image proximity and the object proximity.

Pui=Prox$O$+Prox1

With the same notations, an astigmatism Ast is defined for every gaze direction and for a given object proximity as:

$$Ast = \left|\frac{1}{JT} - \frac{1}{JS}\right|$$

This definition corresponds to the astigmatism of a ray beam created by the lens. It can be noticed that the definition gives, in the primary gaze direction, the classical value of astigmatism. The astigmatism angle, usually called axis, is the angle $\gamma$. The angle $\gamma$ is measured in the frame $\{Q', x_m, y_m, z_m\}$ linked to the eye. It corresponds to the angle with which the image S or T i formed depending on the convention used with relation to the direction $z_m$ in the plane $\{Q', z_m, y_m\}$.

Possible definitions of the optical power and the astigmatism of the lens, in the wearing conditions, can thus be calculated as explained in the article by B. Bourdoncle et al., entitled "Ray tracing through progressive ophthalmic lenses", 1990 International Lens Design Conference, D. T. Moore ed., Proc. Soc. Photo. Opt. Instrum. Eng.

Figure 5:
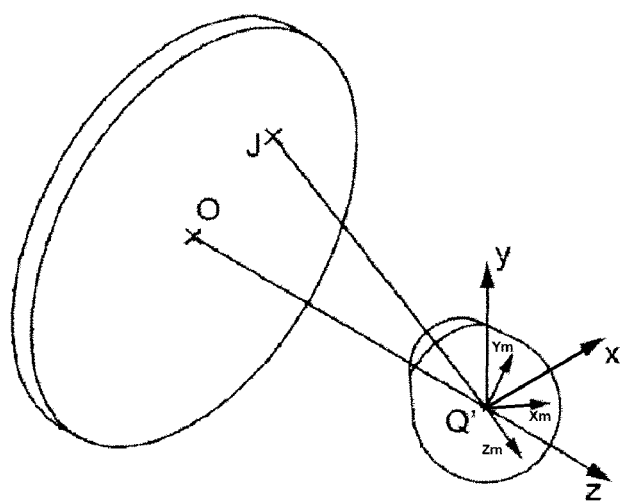
FIG. 5 shows a ray tracing from the center of rotation of the eye.

FIG. 5 represents a perspective view of a configuration wherein the parameters $\alpha$ and $\beta$ are non zero. The effect of rotation of the eye can thus be illustrated by showing a fixed frame $\{x, y, z\}$ and a frame $\{x_m, y_m, z_m\}$ linked to the eye. Frame $\{x, y, z\}$ has its origin at the point Q'. The axis x is the axis Q'O and it is oriented from the lens toward the eye. The y axis is vertical and oriented upwardly. The z axis is such that the frame $\{x, y, z\}$ be orthonormal and direct. The frame $\{x_m, y_m, z_m\}$ is linked to the eye and its center is the point Q'. The $x_m$ axis corresponds to the gaze direction JQ'. Thus, for a primary gaze direction, the two frames $\{x, y, z\}$ and $\{x_m, y_m, z_m\}$ are the same. It is known that the properties for a lens may be expressed in several different ways and notably in surface and optically. A surface characterization is thus equivalent to an optical characterization. In the case of a blank, only a surface characterization may be used. It has to be understood that an optical characterization requires that the lens has been machined to the wearer's prescription. In contrast, in the case of an ophthalmic lens, the characterization may be of a surface or optical kind, both characterizations enabling to describe the same object from two different points of view. Whenever the characterization of the lens is of optical kind, it refers to the ergorama-eye-lens system described above. For simplicity, the term 'lens' is used in the description but it has to be understood as the 'ergorama-eye-lens system'.

The values in optic terms can be expressed for gaze directions. Gaze directions are usually given by their degree of lowering and azimuth in a frame whose origin is the center of rotation of the eye. When the lens is mounted in front of the eye, a point called the fitting cross is placed before the pupil or before the eye rotation center Q' of the eye for a primary gaze direction. The primary gaze direction corresponds to the situation where a wearer is looking straight ahead. In the chosen frame, the fitting cross corresponds thus to a lowering angle $\alpha$ of 0° and an azimuth angle $\beta$ of 0° whatever surface of the lens the fitting cross is positioned—rear surface or front surface.

The above description made with reference to FIGS. 3-5 was given for central vision. In peripheral vision, as the gaze direction is fixed, the center of the pupil is considered instead of center of rotation of the eye and peripheral ray directions are considered instead of gaze directions. When peripheral vision is considered, angle $\alpha$ and angle $\beta$ correspond to ray directions instead of gaze directions.

The wearing conditions are to be understood as the position of the ophthalmic lens with relation to the eye of a wearer, for example defined by a pantoscopic angle, a Cornea to lens distance, a Pupil-cornea distance, a CRE to pupil distance, a CRE to lens distance and a wrap angle.

The Cornea to lens distance is the distance along the visual axis of the eye in the primary position (usually taken to be the horizontal) between the cornea and the back surface of the lens; for example equal to 12 mm.

The Pupil-cornea distance is the distance along the visual axis of the eye between its pupil and cornea; usually equal to 2 mm.

The CRE to pupil distance is the distance along the visual axis of the eye between its center of rotation (CRE) and cornea; for example equal to 11.5 mm.

The CRE to lens distance is the distance along the visual axis of the eye in the primary position (usually taken to be the horizontal) between the CRE of the eye and the back surface of the lens, for example equal to 25.5 mm.

The pantoscopic angle is the angle in the vertical plane, at the intersection between the back surface of the lens and the visual axis of the eye in the primary position (usually taken to be the horizontal), between the normal to the back surface of the lens and the visual axis of the eye in the primary position; for example equal to −8°.

The wrap angle is the angle in the horizontal plane, at the intersection between the back surface of the lens and the visual axis of the eye in the primary position (usually taken to be the horizontal), between the normal to the back surface of the lens and the visual axis of the eye in the primary position for example equal to 0°.

An example of standard wearer condition may be defined by a pantoscopic angle of −8°, a Cornea to lens distance of 12 mm, a Pupil-cornea distance of 2 mm, a CRE to pupil distance of 11.5 mm, a CRE to lens distance of 25.5 mm and a wrap angle of 0°.

Other conditions may be used. Wearing conditions may be calculated from a ray-tracing program, for a given lens.

Figure 6:
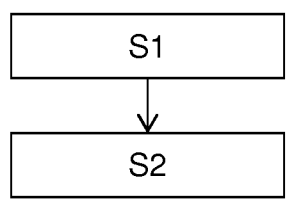
FIG. 6 is an illustration of a chart-flow of an embodiment of the method according to the invention.

As illustrated on FIG. 6, the method according to the invention comprises at least:
- a wearer data providing step S1, and
- a optical function determining step S2.

During the wearer data providing step S1 wearer data are provided.

The wearer data comprise at least an indication of the ophthalmic prescription of the wearer.

Typically, the ophthalmic prescription of the wearer is provided. Alternatively information allowing determining such ophthalmic prescription may be provided, for example an indication allowing determining the ophthalmic prescription of the wearer from a data base and/or lookup table may be provided.

The ophthalmic prescription of a wearer is a set of optical characteristics of optical power, of astigmatism and, where relevant, of addition, determined by an ophthalmologist in order to correct the vision defects of an individual, for example by means of a lens positioned in front of his eye. Generally speaking, the prescription for a progressive addition lens comprises values of spherical power and of astigmatism at the distance-vision point and, where appropriate, an addition value.

According to an embodiment of the invention, the prescription of the wearer comprises a cylinder prescription value and/or a cylinder prescription axis value and/or a sphere prescription value.

Furthermore, the wearer data comprises an indication of the hearing sensitivity of the wearer. Typically, the hearing sensitivity of the wearer is provided. Alternatively information allowing determining such hearing sensitivity may be provided, for example an indication allowing determining the hearing sensitivity of the wearer from a data base and/or lookup table may be provided.

The wearer data may further comprise an indication of the impact of visual indication on the understanding by the wearer of a vocal message, in particular of a speech pronounced by a person facing the wearer.

Typically, the hearing sensitivity of the wearer and/or the impact of visual indication on the understanding by the wearer of a vocal message may be determined by an objective and/or subjective test(s).

While an objective test is based on quantification, usually by a technical device, a subjective test is based on the subjective judgment of an individual faced with the phenomenon being measured and/or provided.

Typically, an audiometry, i.e. a set of measures that determine the audiometric profile of a person, may be carried as indications of the hearing sensitivity of the wearer and/or of the impact of visual indication on the understanding by the wearer of a vocal message. In other words, an audiometry may be carried out to provide precise state of hearing of the wearer.

Among the most common audiometry test, a tonal test and/or a speech frequencies test may be carried out.

Typically, a tone test is carried out by measuring trough air or bone conduction hearing threshold for all speech frequencies, from 125 to 6000 Hz for air conduction and 250 to 4000 Hz for bone transmission.

Air conduction may use a headphone or a speaker, for example place a meter in front of the wearer.

Bone conduction may use vibrator, for example using a tuning fork.

According to an embodiment of the invention, the hearing sensitivity of the wearer may be determined by a test of evaluation of speech understanding in a noisy environment.

There are various tests for evaluating the ability of a person to hear a speech in noisy environment, for example the Acceptable Noise Level Test. An example of such test is provided in "Comparison of Speech Perception in Noise Background With Acceptance of Background Noise in Aided and unaided conditions." Anna K. Nabelek, Joanna W. Tampas, and Samuel B. Burchfield. Journal of Speech, Language, and Hearing Research, October 2004, Vol. 47, 1001-1011.

According to an embodiment of the invention, the hearing sensitivity of the wearer may be determined by a Life Questionnaire concerning the hearing in everyday listening situations.

The Application uHear™ provides an example of such life questionnaire comprising a list of 12 questions an providing based on the answer a score. This questionnaire has been validated scientifically for example in "The Hearing-Dependent Daily Activities Scale to Evaluate Impact of Hearing Loss in Older People". Lopez-Torres Hidalgo J, et al. Ann Fam Med. 2008 September; 6 (5): 441-447.

According to an embodiment of the invention, the hearing sensitivity of the wearer may be determined by a Labo-facial reading test.

The term "labo-facial reading" refers to the understanding of the speech of a person by visually interpreting the movements of the face of said person, and in particular the movements of the lips and the tongue of said person. For instance, the labo-facial reading comprises the lip-reading, also called speech-reading, which corresponds to the understanding of the speech of a person by visually interpreting the movements of the lips of said person.

Typically, it is possible to quantify the intelligibility thanks to softwares which offer training in lip reading using video footage of life in the presence or absence of visual indications. With such softwares it is possible to evaluate a loss or gain based on the visual performance and/or hearing and sound environment (SNR).

The GERIP™ lip reading software (Réf.VS01) may be used to such Labo-facial reading test.

The indication of hearing sensitivity of the wearer may provide different results. For example, the wearer hearing sensitivity may reveal an abnormal loss of sensitivity (meaning that wearer hearing sensitivity is under standard hearing sensitivity), may reveal a normal loss of hearing sensitivity, for example linked to the aging of the wearer, or may reveal a possible gain hearing sensitivity linked to a gain of intelligibility (whether the wearer as abnormal loss or a normal loss of hearing sensitivity) when the wearer has better visualization of labo-facial indication.

For all these cases, it can be proposed to the wearer a specific optical solution as proposed in S2 instead of standard optical solution, and this solution will particularly recommended when the wearer has abnormal hearing sensitivity or when the labo-facial reading test show an important gain.

During the optical function determining step S2, an optical function of an ophthalmic lens adapted to the wearer is determined based at least on the wearer data, i.e. the indication of the hearing sensitivity of the wearer and the indication of the ophthalmic prescription of the wearer.

Typically, based on the wearer data, the lens designer is able to provide an adapted optical function so as to provide ophthalmic correction and improve the hearing of the wearer, in particular the understanding of vocal message, such as speech provided by a person facing the wearer.

According to an embodiment of the invention, during the optical function determining step the optical function comprises a zone adapted for facilitating labo-facial reading of the wearer.

For example, the lens designer may provide a progressive ophthalmic lens having an expanded intermediate distance vision zone. The intermediate distance vision zone corresponds to a zone or area of the ophthalmic lens adapted for intermediate distance vision, for example between 70 cm and 200 cm.

Enlarging the intermediate distance vision zone thus allows the wearer to have a better vision for lip reading: few aberrations in the area, wide area allowing being less dependent on the position/direction of gaze when looking at his interlocutor.

This solution may be based on an optimization of a progressive ophthalmic design in the intermediate distance vision zone thereby improving the performance acuity or contrast sensitivity or perception of curvature and/or movement.

This optimization takes into account the ametropia and wearing conditions.

The optical function determining step may comprise a selection step during which an optical function is selected from a set of predefined optical functions based on said wearer data.

For example, based on the ophthalmic prescription of the wearer, an adapted set of optical surfaces that combined provides a predefined optical function selected from a set of predefined optical functions thanks to any known selection method. Based on the hearing sensitivity of the wearer an adapted modifying surface is selected. The selected modifying surface is to be added to at least one surface of the adapted set of optical surfaces so as to modify the optical function of the ophthalmic lens in order to expand the intermediate distance vision zone.

Figure 7A:
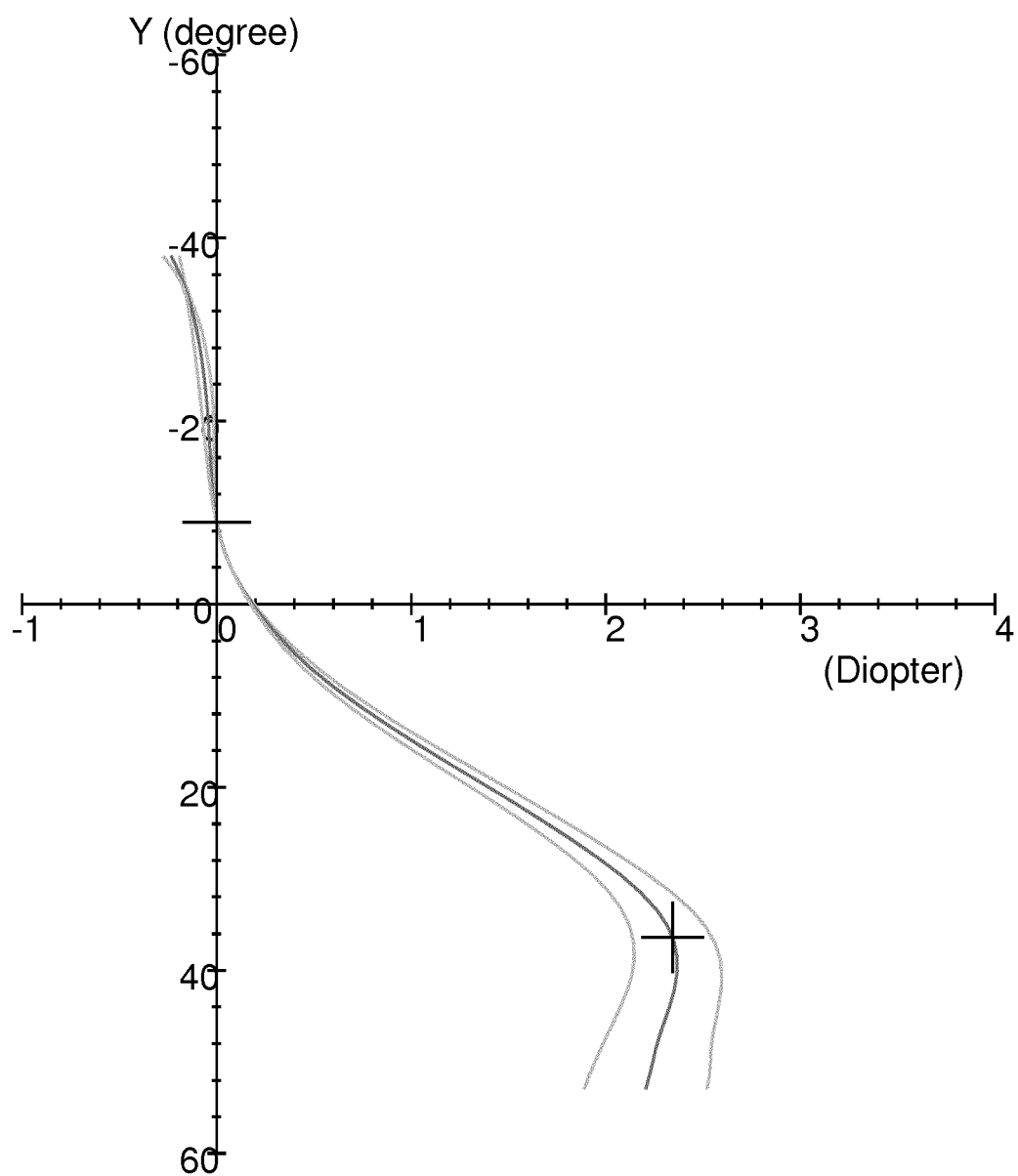
FIGS. 7a and 7b illustrate an example of prior art progressive optical function.
Figure 7B:
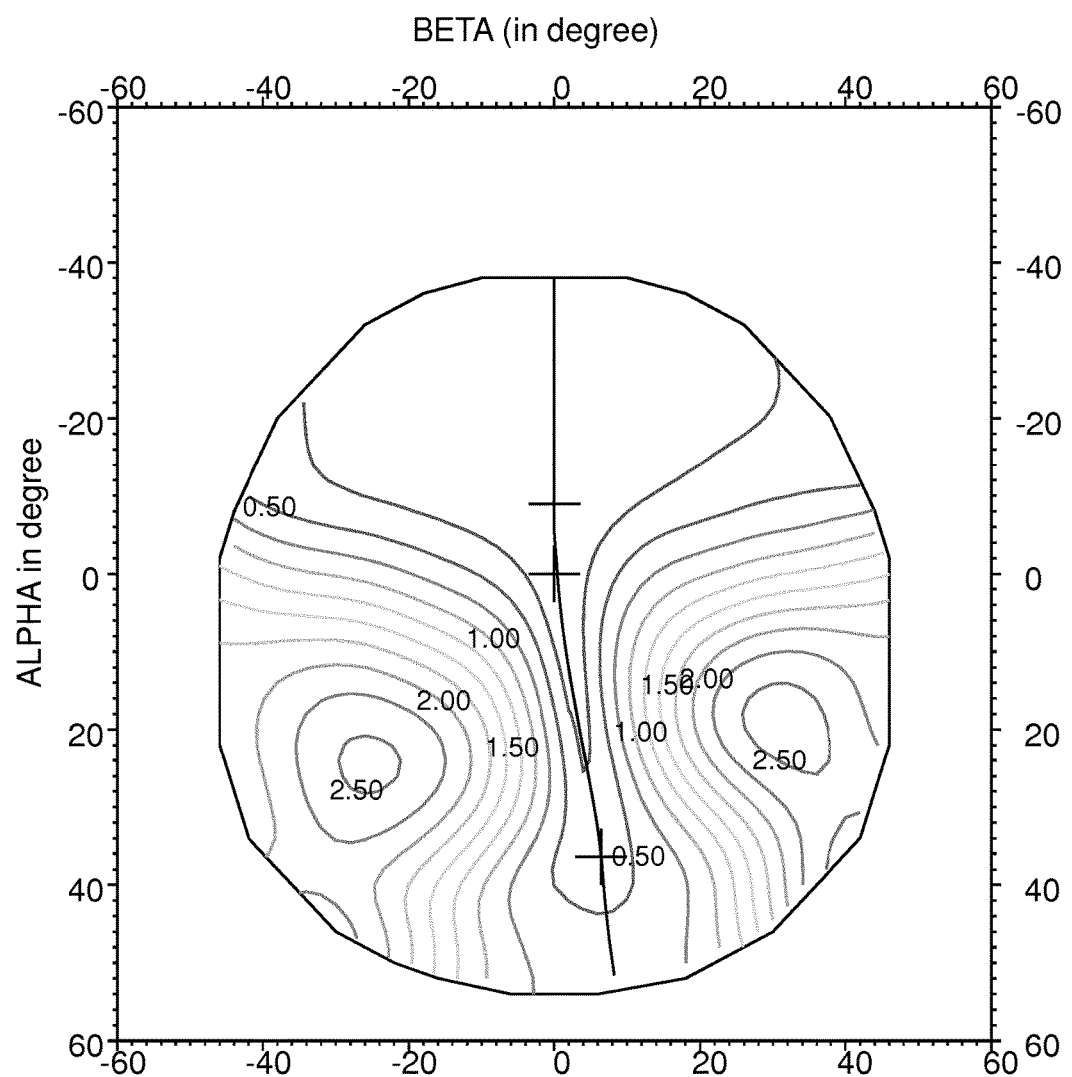

FIGS. 7a and 7b show the optical features of a prior art progressive addition lens with a far vision optical power of 1.0 D and an addition of 2D in standard wearing conditions.

FIG. 7a shows mean optical power surrounded by minimum and maximum optical power curves, along the meridian. The x-axes are graduated in diopters, and the y-axes give the height, in degrees, on the lens, corresponding to the alpha angle.

FIG. 7b shows lines of equal astigmatism, i.e. lines formed by points for which the astigmatism has an identical value. The x-axis and y-axis give the spatial coordinates in degrees.

Figure 8A:
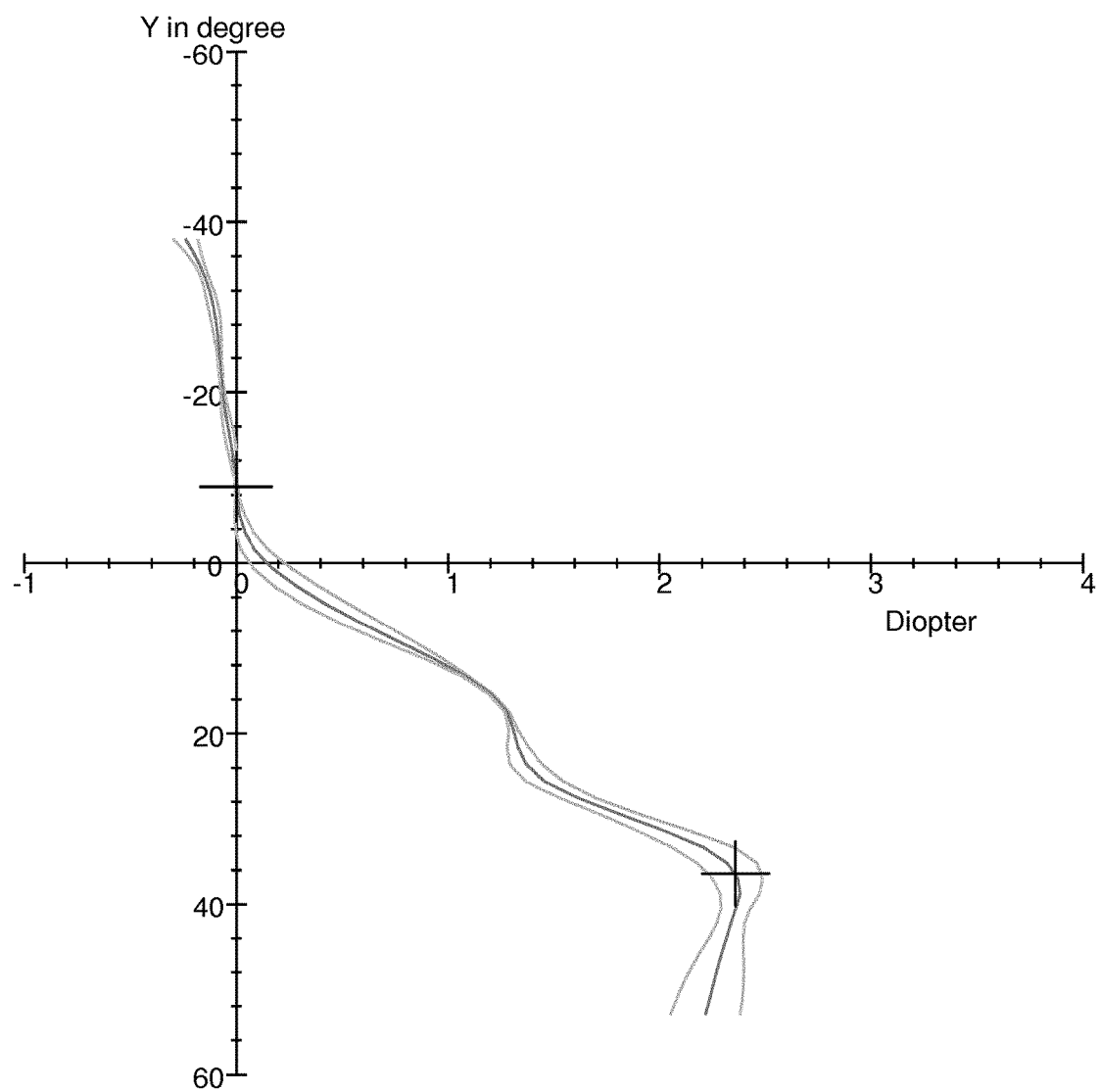
FIGS. 8a, 8b, 9a and 9b illustrate examples of implementation of the method according to the invention.
Figure 8B:
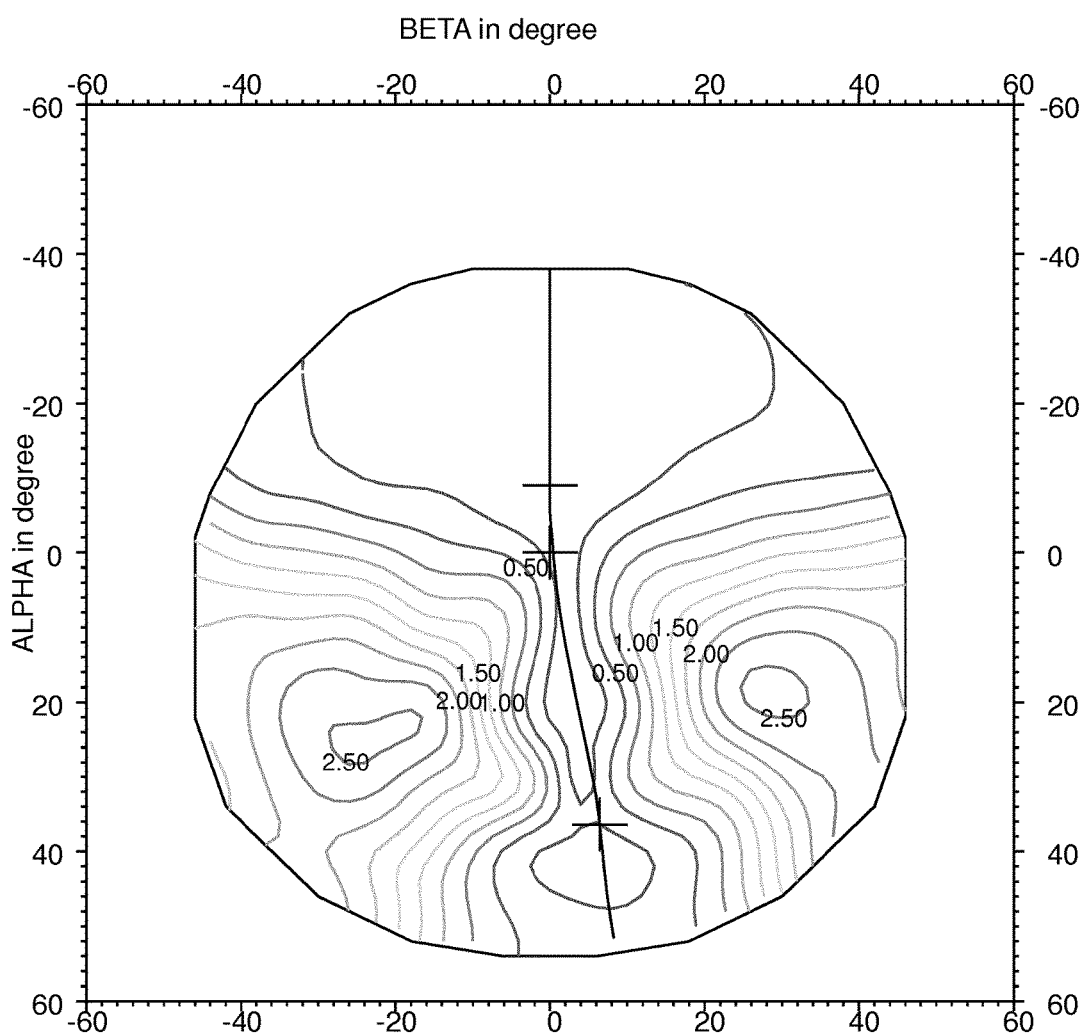

FIGS. 8a and 8b show the optical features of a progressive addition lens with a far vision optical power of 1.0 D and an addition of 2D having an intermediate distance vision zone adapted for facilitating the labo-facial reading of the wearer in the same standard wearing conditions as in FIGS. 7a and 7b.

FIG. 8a shows mean optical power curve surrounded by minimum and maximum optical power curves, along the meridian. The x-axes are graduated in diopters, and the y-axes give the height, in degrees, on the lens.

FIG. 8b shows lines of equal astigmatism, i.e. lines formed by points for which the astigmatism has an identical value. The x-axis and y-axis give the spatial coordinates in degrees.

As illustrated on FIGS. 8a, 8b the modified dioptric function has around ALPHA=18° an enlarged intermediate distance vision zone. Typically, the distance between the astigmatism iso lines 0.5 are distant of 12° whereas in the prior art design such iso lines are distant of 6° around ALPHA=18°.

According to a further embodiment of the invention, to increase the visual comfort of the wearer, especially for advanced presbyopia, one can determine an optical function with a progression that starts earlier or with a steeper slope in order to provide a superior addition than of a conventional progressive optical function for a slightly lowered gaze direction corresponding to the labo-facial direction.

Advantageously, the wearer is able to reach the intermediate distance vision zone matching with labo-facial direction with less vertical head movement.

Figure 9A:
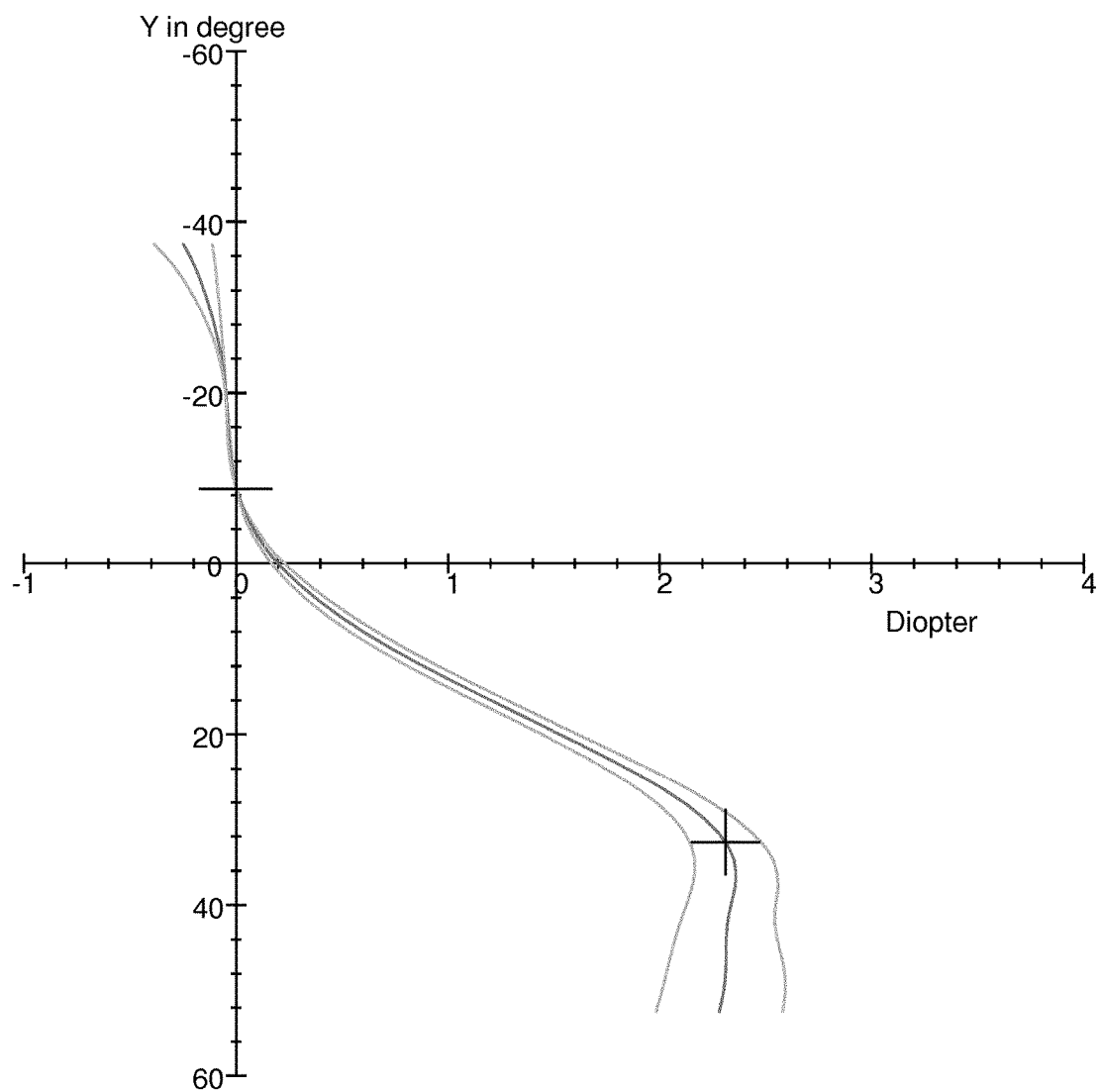
Figure 9B:
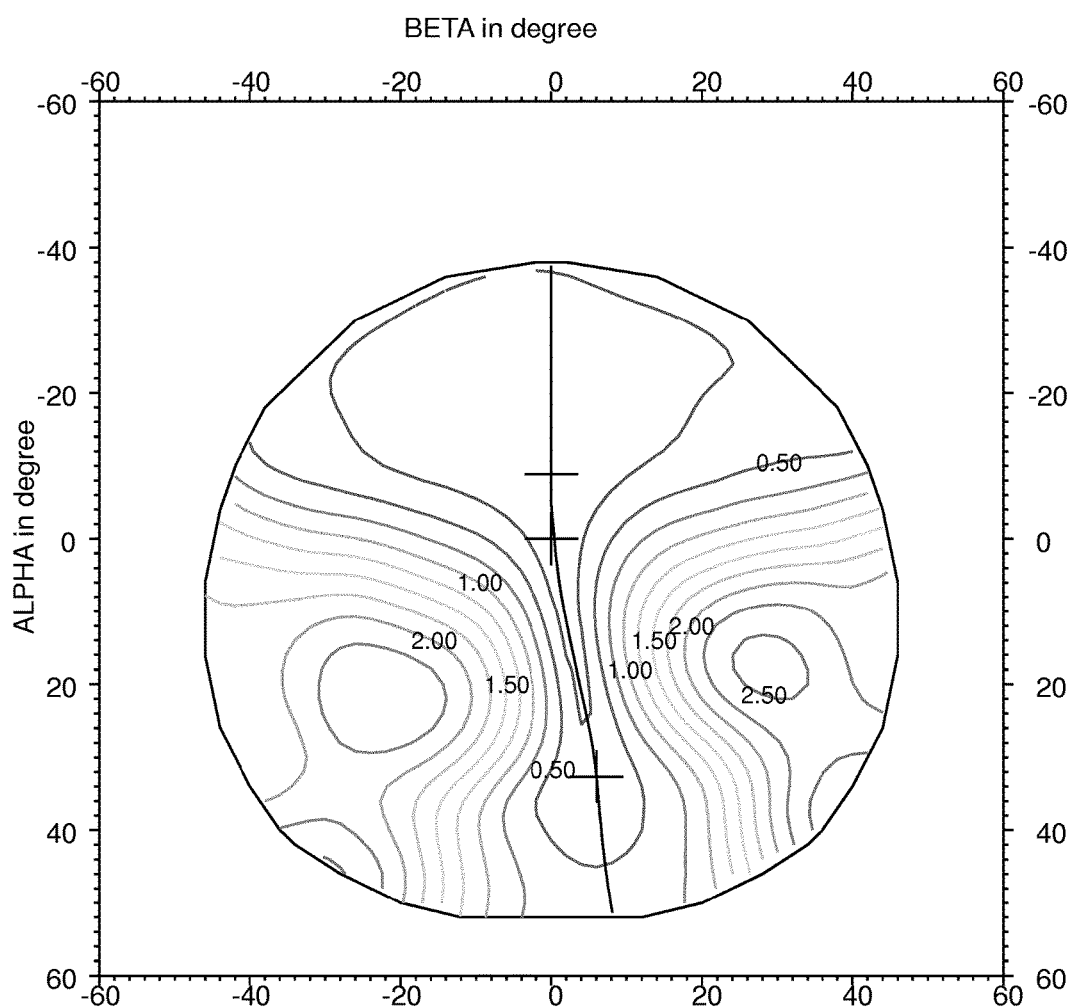

FIGS. 9a and 9b show the optical features of such a progressive addition lens with a far vision sphere of 1.0 D and an addition of 2D in the same standard wearing conditions as in FIGS. 7a and 7b FIG. 9a shows mean optical power curve surrounded by minimum and maximum optical power curves, along the meridian. The x-axes are graduated in diopters, and the y-axes give the height, in degrees, on the lens.

FIG. 9b shows lines of equal astigmatism, i.e. lines formed by points for which the astigmatism has an identical value. The x-axis and y-axis give the spatial coordinates in degrees.

Compared to the optical function represented on FIG. 7a, one observes that the progression has a steeper slope allowing the wearer eye to reach more easily the intermediate distance vision zone matching with labo-facial direction.

According to an embodiment of the invention to reduce the aberrations in the labo-facial direction, one can provide an optical function with a progression starting lower, for example between 1 mm and 4 mm lower than for conventional progressive ophthalmic lenses, for example 2 mm lower, than a conventional progressive optical function. In other words, the far vision zone would be expended so that it also covers the labo-facial direction. This would be especially dedicated to young people with presbyopia having an accommodation greater than 1D which could follow the movement of the lips during a conversation without having to adjust the position of the head in an intermediate distance vision zone.

According to an embodiment of the invention a single vision optical function adapted for intermediate distance vision may be provided. Advantageously, an ophthalmic lens with such optical function provides a wide field of view at 1 m and is particularly suited for labo-facial vision.

According to an embodiment of the invention an ophthalmic lens having an optical function with a small addition (≤1 dp) may be provided. Such an embodiment enables non-presbyopics who have loss of hearing sensitivity to better perceive at communication distance, for example at a distance between 60 cm and 1 m while relieving their accommodation.

According to an embodiment of the invention, the optical function may be provided by an active power lens, for example using an activable power area in the ophthalmic lens adapted for intermediate vision, this power providing addition power when needing to get better visibility of labo-facial indication (for example when having a discussion with a person) and being desactivated otherwise.

Furthermore, such solution is also be interesting for normal hearing wearers, in order to increase their audio visual comfort, even for preventive purposes.

According to an embodiment of the invention, the optical function determining step may comprise a step of determining a transmission function based on said wearer data.

Typically, an ophthalmic lens can be tinted to enhance the contrast of the lips when seen through the ophthalmic lens.

For example red colors may be enhanced. Therefore, the wavelengths corresponding to the red light lambda greater than 650 nm are not absorb whereas other wavelengths between 380 nm and 650 are absorb for example by providing an orange filter.

Alternatively, the red color of the lips may be absorbed by providing a red-absorbing filter between 650 and 780 nm such as a green filter.

These filter may have a slight tint, for example category 0-1 for example according to the ISO8980-3 standard, to preserve the aesthetics of the lens. The color may be further localized in the lens for example in the upper part or the ophthalmic lens may be provided with a gradient.

Tinted solar, polarized, photochromic, electrochromic lenses may further be provided to optimize the intermediate distance vision zone favoring the labo-facial reading. For example by providing a bi-gradient, far and near distance vision zones dark and clear intermediate distance vision zone.

The invention further relates to a pair of ophthalmic lenses adapted for a wearer, wherein at least one of lenses is has an optical function determined by a method according the invention.

Such ophthalmic lenses may be manufactured using standard manufacturing method and device or may be active ophthalmic lenses whose optical function may be adapted for increasing the understanding by the wearer of the ophthalmic lens of a vocal message.

Typically, the invention may relate to programmable lens device comprising a programmable lens, an optical function controller, a memory and a processor. The programmable lens has an optical function and extending between at least one eye of the wearer and the real world scene when the device is used by the wearer. The optical function controller is arranged to control the optical function of the programmable lens. The memory comprises program instructions executable by at the processor to execute the step of the method of the invention.

The invention has been described above with the aid of embodiments without limitation of the general inventive concept. In particular Many further modifications and variations will suggest themselves to those skilled in the art upon making reference to the foregoing illustrative embodiments, which are given by way of example only and which are not intended to limit the scope of the invention, that being determined solely by the appended claims.

In the claims, the word "comprising" does not exclude other elements or steps, and the indefinite article "a" or "an" does not exclude a plurality. The mere fact that different features are recited in mutually different dependent claims does not indicate that a combination of these features cannot be advantageously used. Any reference signs in the claims should not be construed as limiting the scope of the invention.

The invention claimed is:

1. A method implemented by at least one processor for determining an optical function of an ophthalmic lens adapted to a wearer, the method comprising:

obtaining wearer data at least including first information related to a hearing sensitivity of the wearer and second information related to an ophthalmic prescription of the wearer;

determining an optical function adapted to the wearer based at least on the wearer data; and obtaining optical function data corresponding to the determined optical function for manufacturing the ophthalmic lens consistent with the optical function data.

2. The method according to claim 1, wherein the wearer data further includes third information related to an impact of visual indication on an understanding by said wearer of a vocal message.

3. The method according to claim 1, wherein said determining is carried out so that said optical function includes a zone adapted for facilitating labo-facial reading of the wearer.

4. The method according to claim 1, wherein the first information related to the hearing sensitivity of the wearer is determined by at least an objective type test.

5. The method according to claim 4, wherein said objective type test is a perception test of a range of tonal frequencies.

6. The method according to claim 4, wherein said objective type test is a perception test of a range of vocal frequencies.

7. The method according to claim 1, wherein the first information related to the hearing sensitivity of the wearer is determined by at least a subjective type test.

8. The method according to claim 7, wherein said subjective type test is chosen among one of the following tests consisting of: an evaluation of speech understanding in a noisy environment a Life Questionnaire concerning hearing in everyday listening situations and a Labo-facial reading test.

9. The method according to claim 1, wherein said determining further includes selection of an optical function from a set of predefined optical functions based on said wearer data.

10. The method according to claim 1, wherein said determining further includes determining a transmission function based on said wearer data.

11. The method according to claim 1, wherein said determining further includes determining a dioptric function based on said wearer data.

12. The method according to claim 1, wherein the ophthalmic lens is a lens of a pair of ophthalmic lenses adapted for the wearer.

13. A non-transitory computer readable medium comprising one or more stored sequences of instructions that are accessible to a processor and which, when executed by the processor, causes the processor to carry out a method for determining an optical function of an ophthalmic lens adapted to a wearer, the method comprising:

obtaining wearer data at least including first information related to a hearing sensitivity of the wearer and second information related to an ophthalmic prescription of the wearer;

determining an optical function adapted to the wearer based at least on the wearer data; and obtaining optical function data corresponding to the determined optical function for manufacturing said ophthalmic lens consistent with the optical function data.

14. The non-transitory computer readable medium of claim 13, wherein the ophthalmic lens comprises at least a zone adapted for intermediate distance vision, and wherein the computer readable medium further comprises one or more stored sequences of instructions, which when executed by the processor, causes the processor to use the at least one zone to increase an understanding by the wearer of the ophthalmic lens of a vocal message.

15. The computer readable medium of claim 13, further comprising one or more stored sequences of instructions, which when executed by the processor, causes the processor to obtain third information related to an impact of visual indication on an understanding by said wearer of a vocal message, wherein the wearer data comprises the third information.

* * * * *